United States Patent
Igarashi

(10) Patent No.: US 10,145,780 B2
(45) Date of Patent: Dec. 4, 2018

(54) THREAD PLUG GAUGE WITH MAINTENANCE LINE, THREAD RING GAUGE, AND METHOD OF MANUFACTURING THE SAME

(71) Applicant: NIIGATA SEIKI CO., LTD., Tokyo (JP)

(72) Inventor: Toshiyuki Igarashi, Tokyo (JP)

(73) Assignee: NIIGATA SEIKI CO., LTD., Tokyo (JP)

( * ) Notice: Subject to any disclaimer, the term of this patent is extended or adjusted under 35 U.S.C. 154(b) by 481 days.

(21) Appl. No.: 14/972,548

(22) Filed: Dec. 17, 2015

(65) Prior Publication Data

US 2016/0103060 A1   Apr. 14, 2016

Related U.S. Application Data

(62) Division of application No. 14/170,357, filed on Jan. 31, 2014, now Pat. No. 9,372,146.

(30) Foreign Application Priority Data

Apr. 3, 2013   (JP) ................................. 2013-077351

(51) Int. Cl.
| | |
|---|---|
| *G01N 19/00* | (2006.01) |
| *G01B 3/34* | (2006.01) |
| *G01B 3/36* | (2006.01) |
| *B41M 5/20* | (2006.01) |
| *G01B 3/48* | (2006.01) |
| *G01B 5/20* | (2006.01) |

(52) U.S. Cl.
CPC ............... *G01N 19/00* (2013.01); *B41M 5/20* (2013.01); *G01B 3/34* (2013.01); *G01B 3/36* (2013.01); *G01B 3/48* (2013.01); *G01B 5/204* (2013.01); *G01N 2203/0629* (2013.01)

(58) Field of Classification Search
CPC ............. G01N 19/00; G01B 3/36; G01B 3/34
USPC ............................ 33/501.45, 199 R; 116/208
See application file for complete search history.

(56) References Cited

U.S. PATENT DOCUMENTS

| | | | |
|---|---|---|---|
| 2,000,535 A | 5/1935 | Peisch | |
| 3,057,072 A | 10/1962 | Werner | |
| 4,213,247 A * | 7/1980 | Romine | G01B 3/36 33/199 R |
| 5,134,783 A * | 8/1992 | Perry | G01B 3/36 33/199 R |
| 9,534,881 B2 * | 1/2017 | Igarashi | G01B 3/34 |

(Continued)

FOREIGN PATENT DOCUMENTS

| | | |
|---|---|---|
| JP | 55161201 U | 11/1980 |
| JP | 62195704 U | 12/1987 |

*Primary Examiner* — Christopher W Fulton
(74) *Attorney, Agent, or Firm* — Holtz, Holtz & Volek PC

(57) ABSTRACT

A thread gauge, which allows to reliably know the time for replacement by visual checking and improves the predetermined dimensional accuracy of a thread product has a go-side thread measuring portion extending from one side of a shank portion coaxially with the shank portion or a not-go-side thread measuring portion extending from an other side of the shank portion coaxially with the shank portion, a wear checking gauge line having a predetermined length and a predetermined depth formed on male thread portions and female thread portions formed on the go-side thread measuring portion or the not-go-side thread measuring portion.

5 Claims, 25 Drawing Sheets

(56) References Cited

U.S. PATENT DOCUMENTS

2005/0241166 A1 11/2005 Porter
2010/0281700 A1* 11/2010 Wu .................... G01B 3/48
　　　　　　　　　　　　　　　　　　　　33/199 R
2012/0132129 A1 5/2012 Edmond

* cited by examiner

【Fig. 1】
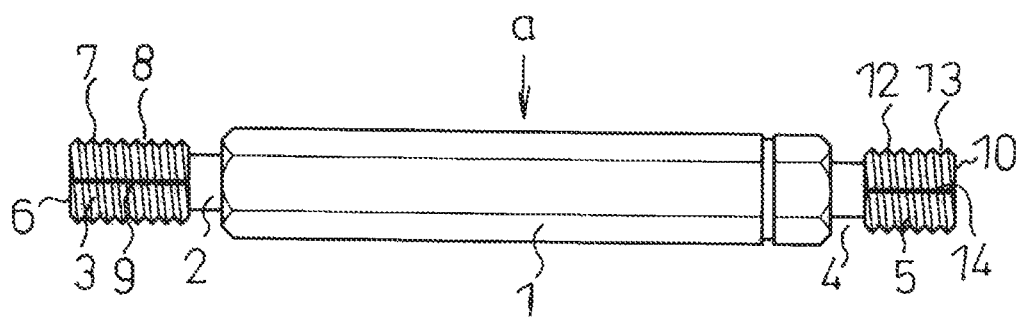

[Fig. 2]
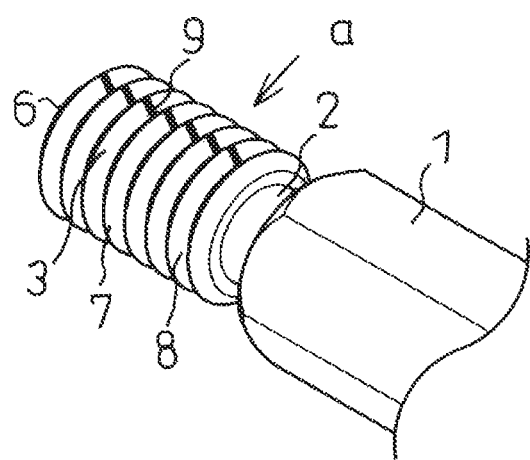

[Fig. 3]
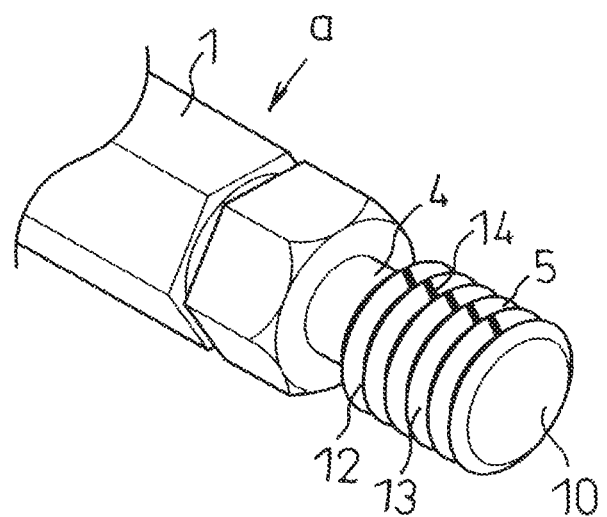

[Fig. 4]
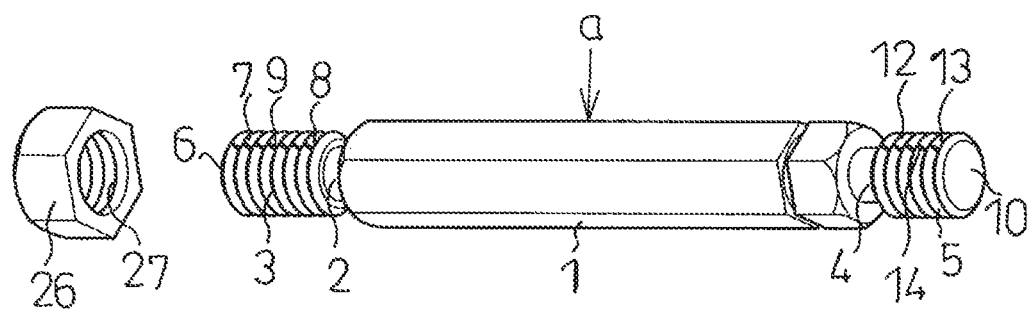

[Fig. 5]
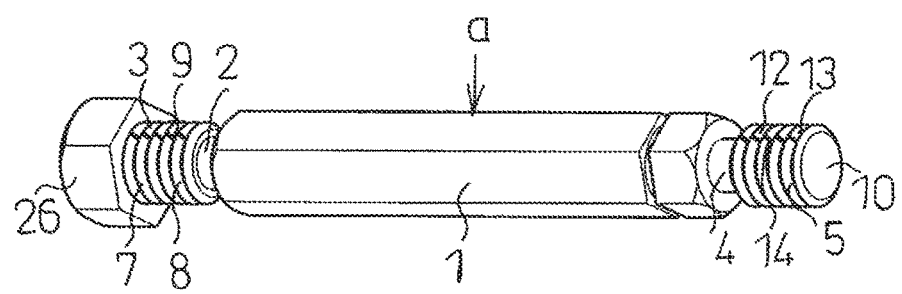

[Fig. 6]
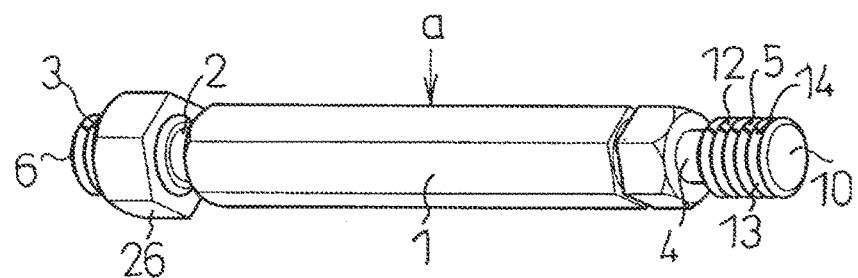

[Fig. 7]
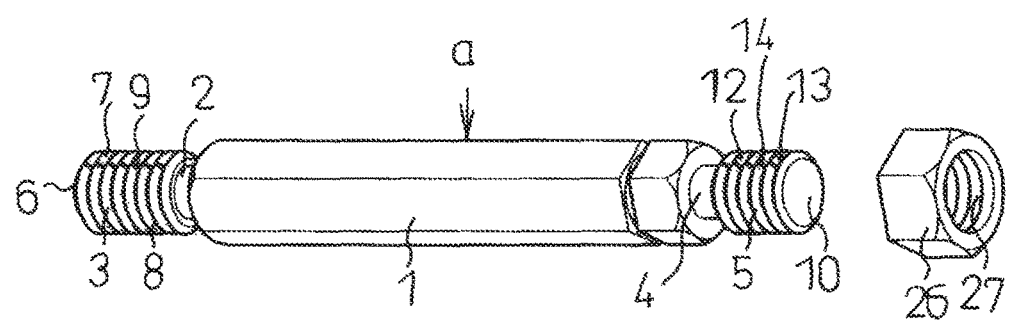

【Fig. 8】
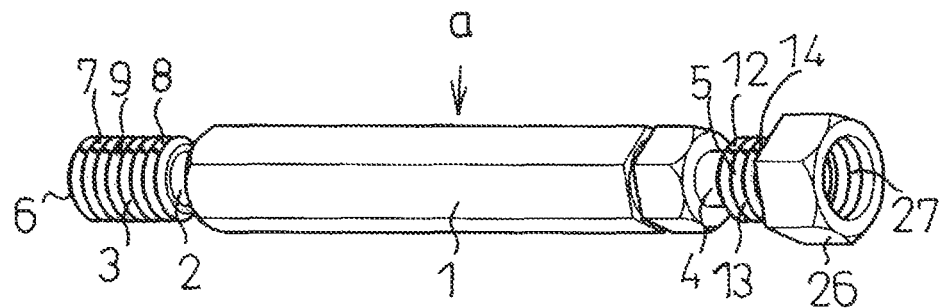

【Fig. 9】
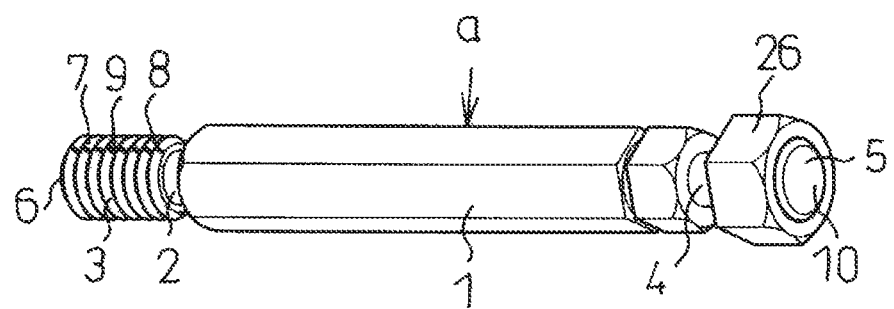

[Fig. 10]
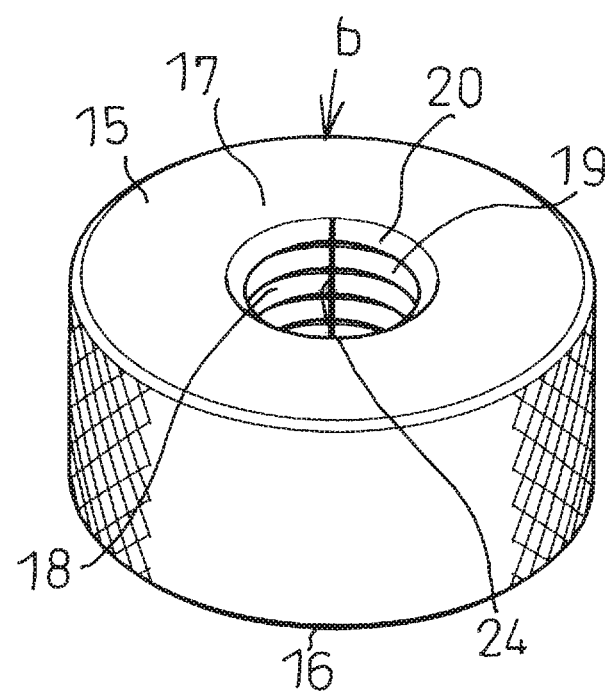

[Fig. 11]
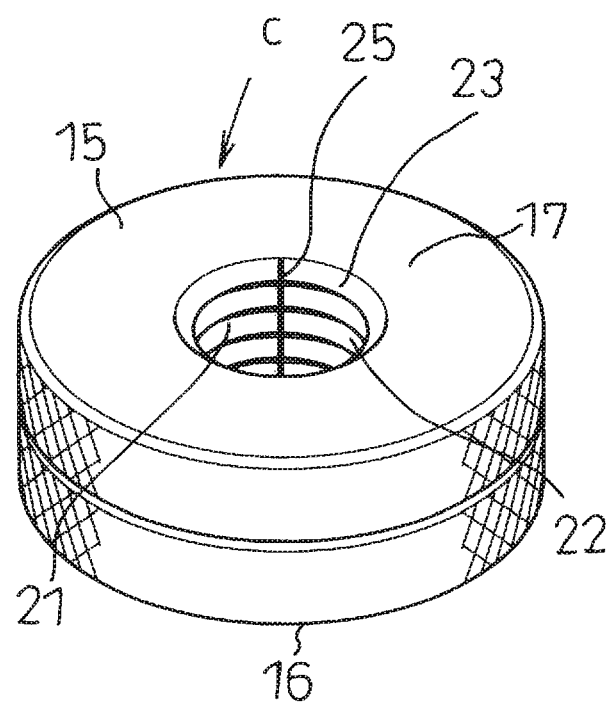

[Fig. 1 2]
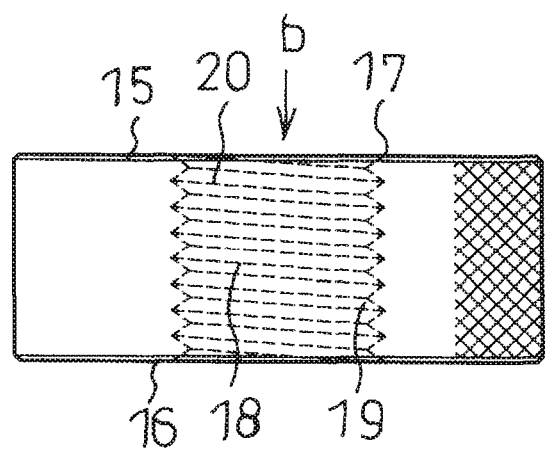

[Fig. 13]
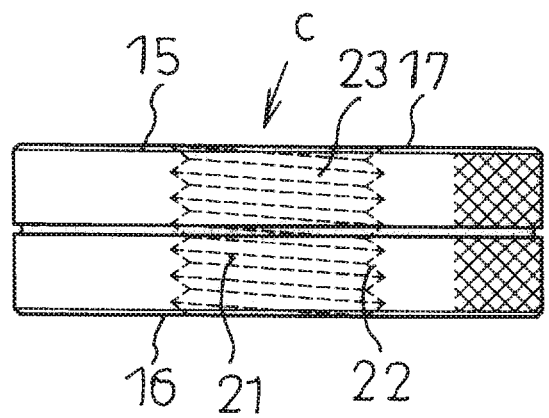

[Fig. 14]
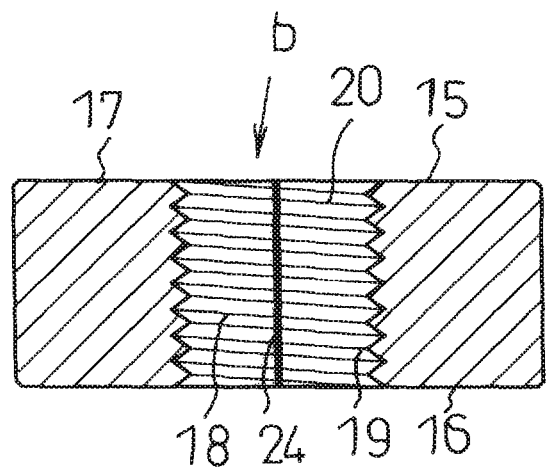

[Fig. 15]
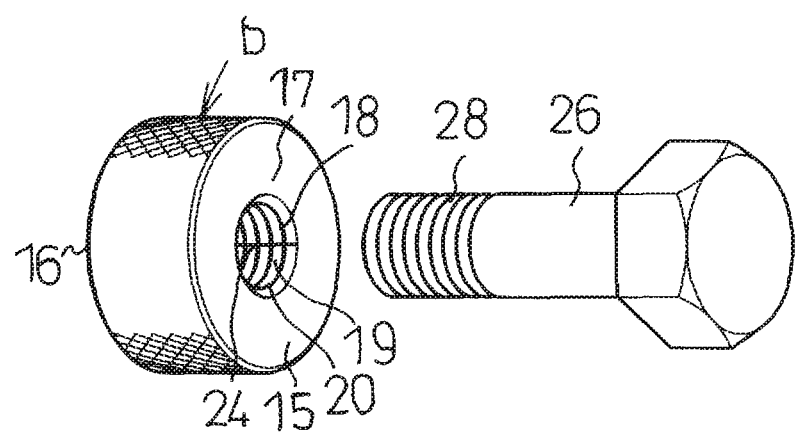

【Fig. 16】
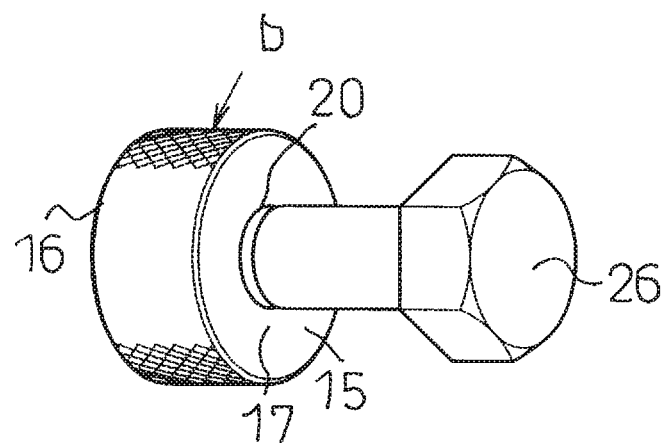

【Fig. 17】
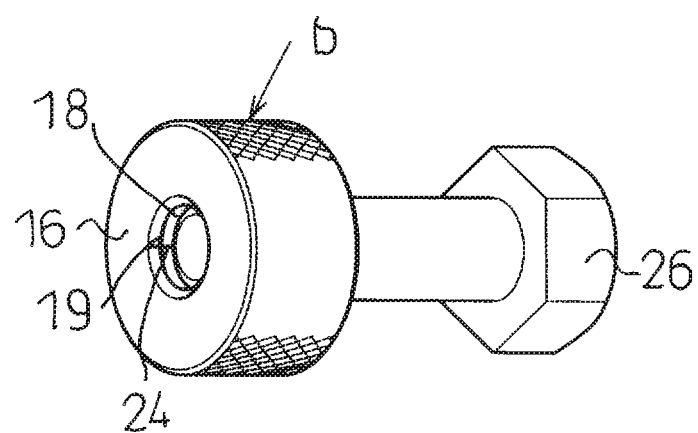

【Fig. 18】
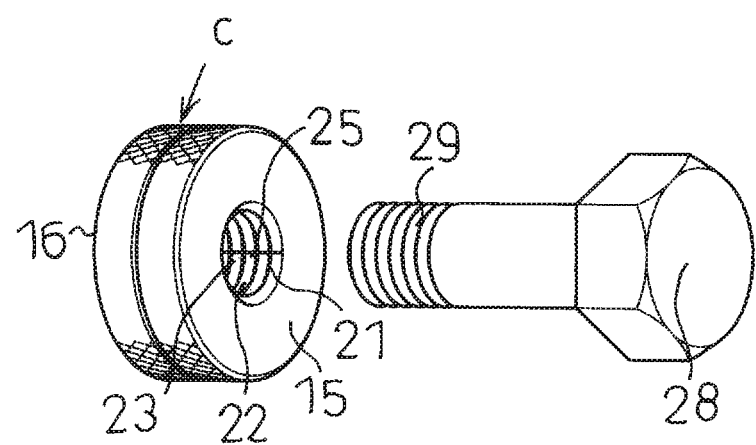

[Fig. 19]
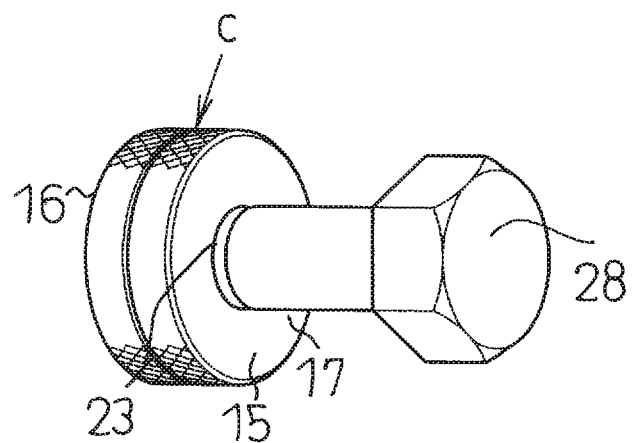

[Fig. 20]
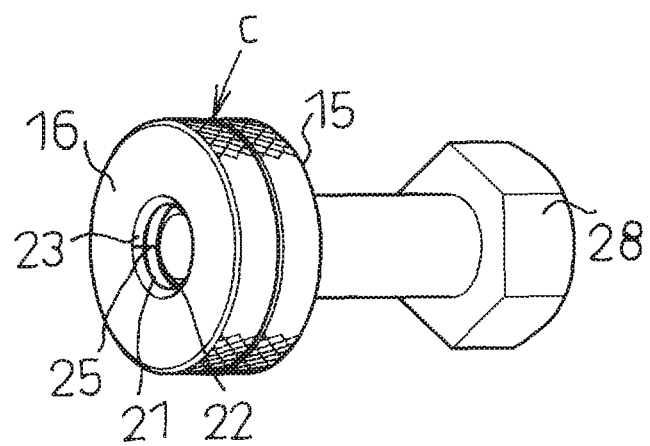

[Fig. 21]
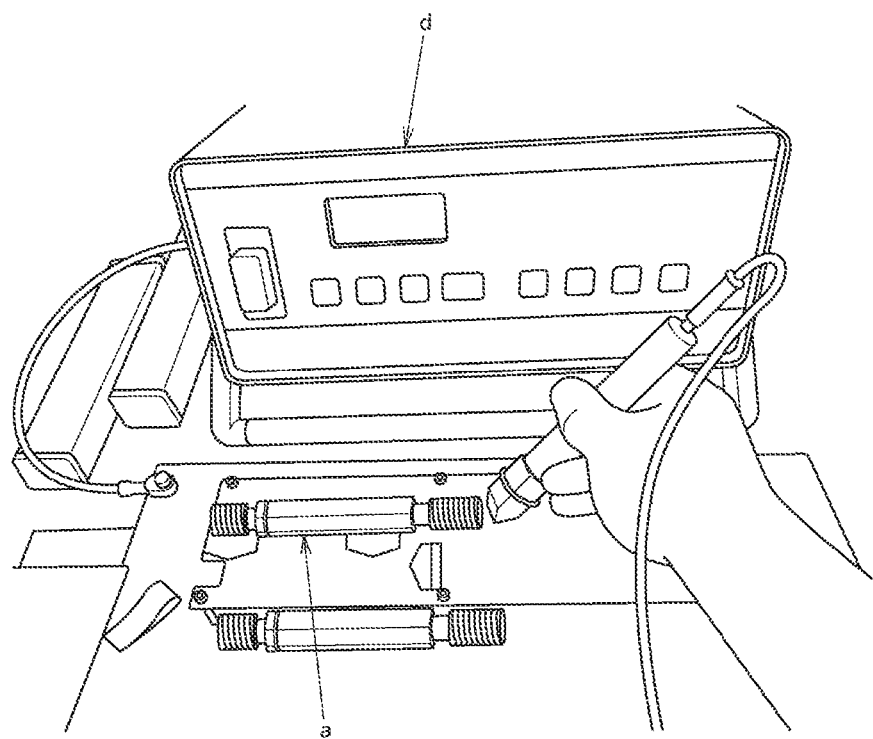

[Fig. 22]
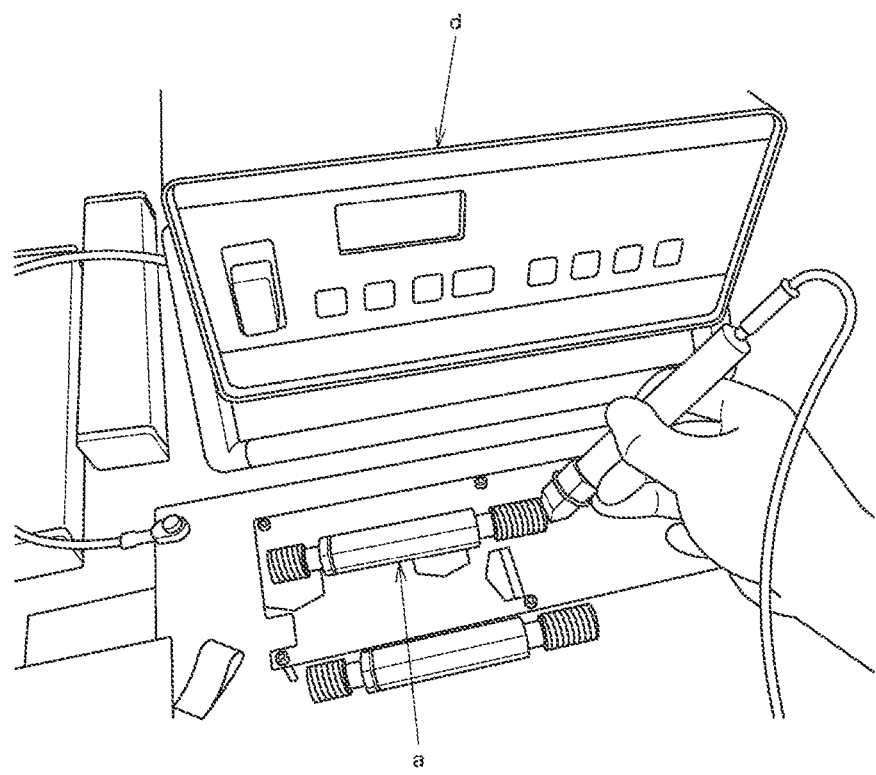

【Fig. 23】
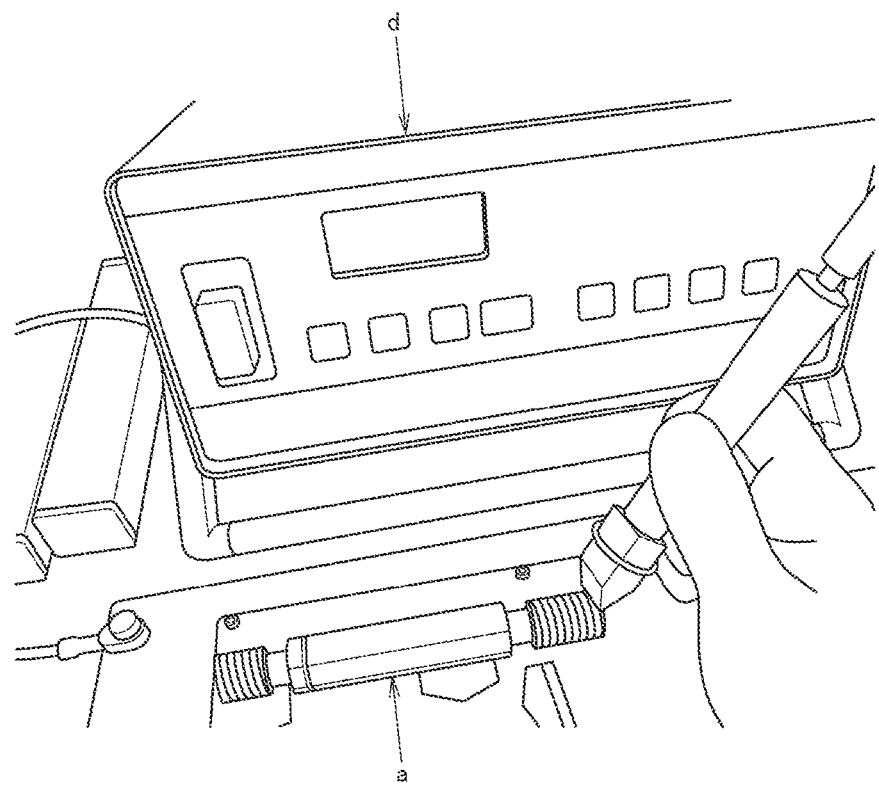

【Fig. 2 4】
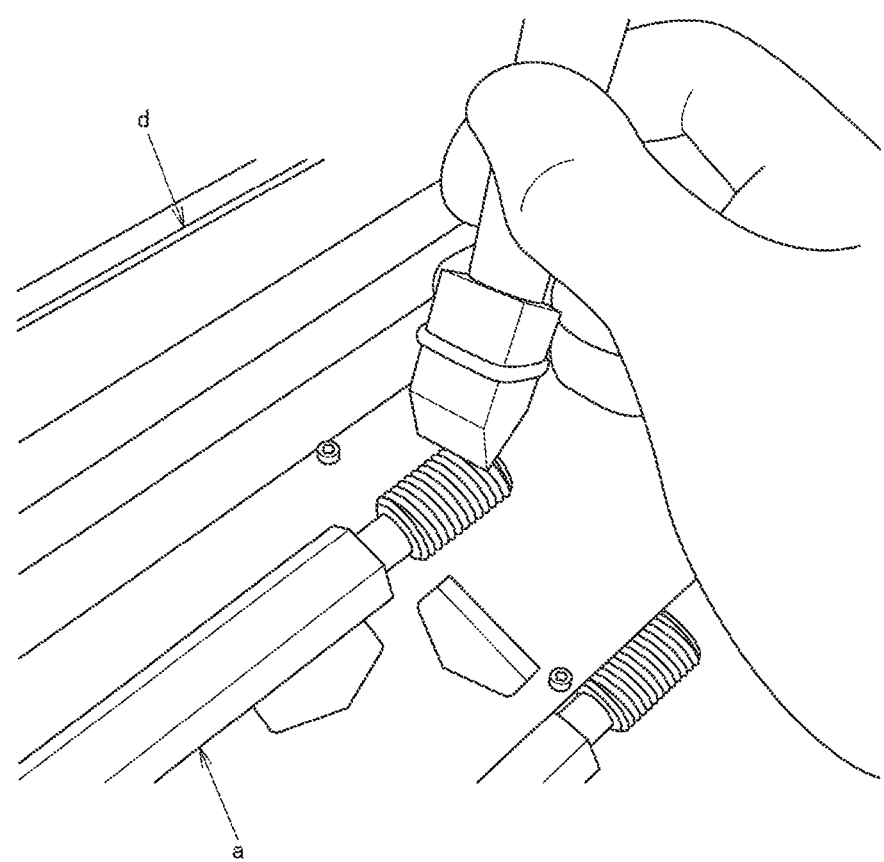

【Fig. 25】
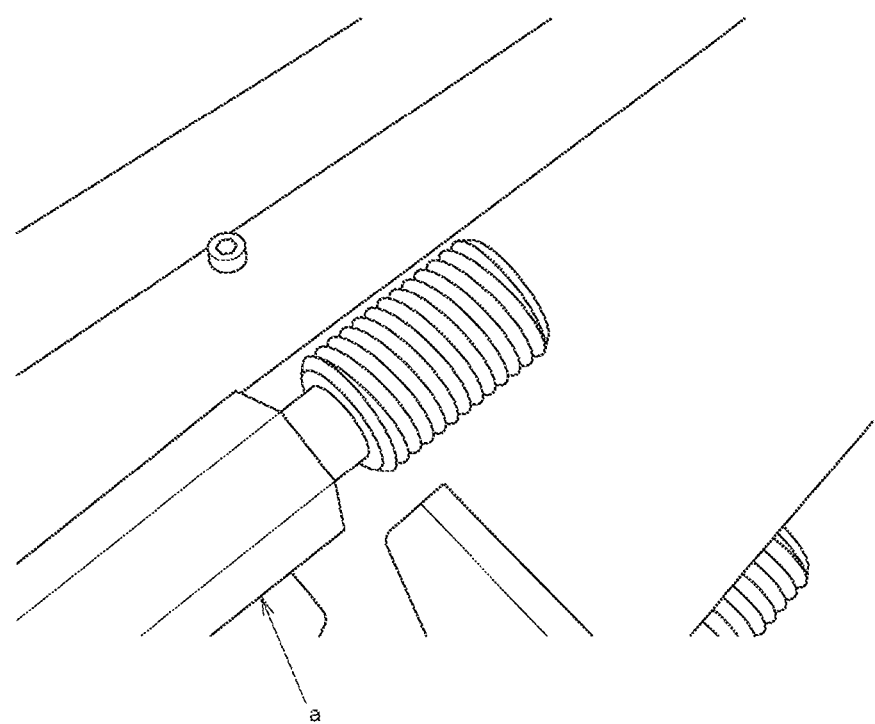

THREAD PLUG GAUGE WITH MAINTENANCE LINE, THREAD RING GAUGE, AND METHOD OF MANUFACTURING THE SAME

CROSS-REFERENCE TO RELATED APPLICATIONS

This is a Divisional of U.S. application Ser. No. 14/170,357, filed Jan. 31, 2014, (now U.S. Pat. No. 9,372,146), which is based upon and claims the benefit of priority from prior Japanese Patent Application No. 2013-077351, filed Apr. 3, 2013, the entire contents of both of which are incorporated herein by reference.

FIELD OF THE INVENTION

The present invention relates to a thread plug with a maintenance line or the like and thread ring gauge which allow to accurately and reliably know the times for replacement of various types of thread gauges and reliably and quickly manufacture thread plug gauges and thread ring gauges by forming, in advance, wear checking gauge lines or round points on the male and female thread portions of go-side thread measuring portions and not-go-side thread measuring portions forming various types of thread gauges and letting the gauge lines or round points wear out and disappear due to contact because of repeated insertion and removal between the various types of thread gauges and various types of test products, and a method of manufacturing the same.

DESCRIPTION OF THE RELATED ART

Conventionally, Utility Model Application Publication No. 62/195,704 discloses a thread gauge.

The thread gauge disclosed in this patent literature has a wear-resistant film formed on the surface of each male thread portion, with the film having a color different from that of each male thread portion. Providing this thread gauge makes it possible to facilitate visually checking the time for replacement of the thread gauge and to perform precise and economical inspection of female thread products and repair the thread gauge by regenerating a wear-resistant film.

Utility Model Application Publication No. 55/161,201 discloses a ring gauge.

A characteristic feature of this ring gauge is that the thread portion, is formed from a refractory metal consisting of 75% to 85% WC and 15% to 20% Co. Based on the material characteristics of this refractory metal, this ring gauge exhibits excellent wear resistance because of high hardness, small friction coefficients with respect to objects to be measured, and a small coefficient of thermal expansion (about ⅓ that of a conventional product) because of being the sintered product. In addition, for example, the ring gauge exhibits a small temporal change in size because of small residual strain. These make it possible to considerably improve the measurement accuracy and tolerance of the ring gauge.

CITATION LIST

Patent Literature

[Patent Literature 1] Utility Model Application Publication No. 62/195,704

[Patent Literature 2] Utility Model Application Publication No. 55/161,201

SUMMARY OF THE INVENTION

Problem that the Invention is to Solve

The male thread gauge disclosed in Utility Model Application Publication No. 62-195704 described above has a wear-resistant film formed on the surface of each male thread portion, with the film having a color different from that of each male thread portion, thereby making it possible to facilitate visually checking the time for replacement of the thread gauge and perform precise and economical inspection of thread products. In contrast to this, the present invention allows to reliably know the times for replacement of thread gauges by visual check by providing wear checking gauge lines, each having a predetermined length and a predetermined depth, on the male and female thread portions of the thread measuring portions of various types of gauges, without forming any wear-resistant film, and can provide a thread gauge product with a higher added value than a conventional thread gauge by improving the predetermined dimensional accuracy of a thread product.

In addition, the present invention can reliably and quickly manufacture the above thread gauge.

The ring gauge disclosed in Utility Model Application Publication No. 55/161,201 described above has been improved in measurement accuracy and tolerance by forming the thread portion using a refractory metal consisting of 75% to 85% WC and 15% to 20% Col. This makes the ring gauge exhibit excellent wear resistance because of high hardness, which is a material characteristic of a refractory metal, small friction coefficients with respect to objects to be measured, and a small coefficient of thermal expansion because of being the sintered product. In addition, for example, the ring gauge exhibits a small temporal change in size because of small residual strain. These make it possible to considerably improve the measurement accuracy and tolerance of the ring gauge.

However, the thread portion of the disclosed ring gauge described above does not allow to easily visually check whether the time for replacement of the ring gauge has come due to wear upon measurement.

In contrast, the present invention allows to reliably know the times for replacement of thread gauges by visual check by providing wear checking gauge lines or round points, each having a predetermined length and a predetermined depth, in advance as described above, on the male and female thread portions forming the respective thread measuring portions, and letting the gauge line or round point disappear upon repeated gauge measurement, and can provide a thread gauge product with a higher added value than a conventional thread gauge by improving the predetermined dimensional accuracy of a thread product.

In addition, the present invention can reliably and quickly manufacture the thread gauge described above.

Means for Solving the Problem

As a means for solving the problem, a first aspect of the invention provides a thread plug gauge with a maintenance line or the like in which in a thread plug gauge body a having a go-side thread measuring portion 3 extending from one side of a shank portion 1 coaxially with the shank portion 1 or a not-go-side thread measuring portion 5 extending from the other side of the shank portion 1 coaxially with the shank portion 1, a wear checking gauge line 9 or 14 having a predetermined length and a predetermined depth or a round point having a predetermined depth and a predetermined diameter is formed on a male thread portion 7 or 12 and a female thread portion 8 or 13 formed on the go-side thread measuring portion 3 or the not-go-side thread measuring portion 5.

As a means for solving the problem, a second aspect of the invention provides a thread plug gauge with a maintenance line or the like in which the wear checking gauge line 9 or 14 formed on the male thread portion 7 or 12 and the female thread portion 8 or 13 of the go-side thread measuring portion 3 or the not-go-side thread measuring portion 5 has a linear shape.

As a means for solving the problem, a third aspect of the invention provides a thread plug gauge with a maintenance line or the like in which the wear checking gauge line 9 or 14 is printed on the male thread portion 7 or 12 and the female thread portion. 8 or 13 so as to have a depth of 0.3 μm to 0.4 μm and a width of 0.2 mm.

As a means for solving the problem, a fourth aspect of the invention provides a thread plug gauge with a maintenance line or the like in which the thread plug gauge with the maintenance line or the like is formed by using alloy tool steel, a ceramic material, or a superhard material.

As a means for solving the problem, a fifth aspect of the invention provides a thread plug gauge with a maintenance line or the like in which the round point, is printed on the male thread portion 7 or 12 and the female thread portion 8 or 13 so as to have a depth of 0.3 μm to 0.4 μm and a diameter of 2 mm.

As a means for solving the problem, a sixth aspect of the invention provides a method of manufacturing a thread plug gauge with a maintenance line or the like, comprising connecting a thread plug gauge body a to a negative electrode base connected to a power supply box b which controls a current, setting a green stencil which has a cut-out portion having a desired marking pattern and from which an electrolytic solution exudes on a carbon filter with the electrolytic solution being contained in a positive electrode handle connected to the power supply box b, energizing the set positive electrode handle while gripping the handle, and forming a wear checking gauge line 3 on a male thread portion 7 and a female thread portion 8 of a go-side thread measuring portion 3 or a male thread portion 12 and a female thread portion 13 of a not-go-side thread measuring portion 5 of the thread plug gauge body a by performing a marking process by sliding the positive electrode handle on the male thread portion 7 and the female thread portion 8 of the go-side thread measuring portion 3 or the male thread portion 12 and the female thread portion 13 of the not-go-side thread measuring portion 5 of the thread plug gauge body a to form a concave shape which has a depth of 0.3 μm to 0.4 μm and a width of 0.2 mm and is blackened.

As a means for solving the problem, a seventh aspect of the invention provides a thread ring gauge with a maintenance line or the like in which in a thread ring gauge body b or c having an upper surface portion 15 and a lower surface portion 16 and having a go-side thread measuring portion 20 formed on an inside portion 17 to have a male thread portion 18 and a female thread portion 19 of the same class as that of a screw to be measured or having a not-go-side thread measuring portion 23 formed on an inside portion 17 to have a male thread portion 21 and a female thread portion 22 of the same class as that of a screw to be measured, wear checking gauge lines 24 and 25 each having a predetermined length and a predetermined depth or round points each having a predetermined depth and a predetermined diameter are formed on male thread portions 18 and 21 and female thread portions 19 and 22 of the go-side thread measuring portion 20 and the not-go-side thread measuring portion 23 which are engraved in an inside portion between the upper surface portion 15 and the lower surface portion 16 which constitute one of the thread ring gauge bodies b and c.

As a means for solving the problem, an eighth aspect of the invention provides a thread ring gauge with a maintenance line or the like in which the wear checking gauge line 24 or 25 of the seventh aspect of the invention has a linear shape.

As a means for solving the problem, a ninth aspect of the invention provides a thread ring gauge with a maintenance line or the like in which the wear checking gauge line 24 or 25 of the seventh aspect of the invention is printed on the male thread portion 18 or 21 and the female thread portion 19 or 22 so as to have a depth of 0.3 μm to 0.4 μm and a width of 0.2 mm.

As a means for solving the problem, a tenth aspect of the invention provides a thread ring gauge with a maintenance line or the like in which the round point is printed on the male thread portion 18 or 21 and the female thread portion 19 or 22 so as to have a depth of 0.3 μm to 0.4 μm and a diameter of 2 mm.

As a means for solving the problem, an eleventh aspect of the invention provides a thread ring gauge with a maintenance line or the like in which the thread ring gauge body b or c is formed by using alloy tool steel, a ceramic material, or a superhard material.

As a means for solving the problem, a twelfth aspect of the invention provides a method of manufacturing a thread plug gauge with a maintenance line or the like, comprising connecting a thread ring gauge body b or c to a negative electrode base connected to a power supply box b which controls a current, setting a green stencil which has a cut-out portion having a desired marking pattern and from which an electrolytic solution exudes on a carbon filter with the electrolytic solution being contained in a positive electrode handle connected to the power supply box b, energizing the set positive electrode handle while gripping the handle, and forming a wear checking gauge line 24 or 25 on a male thread portion 18 and a female thread portion 19 of a go-side thread measuring portion 20 or a male thread portion 21 and a female thread portion 22 of a not-go-side thread measuring portion 23 of the thread ring gauge body b or c by performing a marking process by sliding the positive electrode handle on the male thread portion 18 and the female thread portion 19 of the go-side thread measuring portion 20 or the male thread portion 21 and the female thread portion 22 of the not-go-side thread measuring portion 23 to form a concave shape which has a depth of 0.3 μm to 0.4 μm and a width of 0.2 mm and is blackened, or connecting a thread plug gauge body a to a negative electrode base connected to a power supply box b which controls a current, setting a green stencil which has a cut-out portion having a desired marking pattern and from which an electrolytic solution exudes on a carbon filter with the electrolytic solution being contained in a positive electrode handle connected to the power supply box b, energizing the set positive electrode handle while gripping the handle, and forming a wear checking round point on a male thread portion 7 and a female thread portion 8 of a go-side thread measuring portion 3 or a male thread portion 12 and a female thread portion 13 of a not-go-side thread measuring portion 5 of the thread plug gauge body a by performing a marking process without sliding the positive electrode handle on the male thread portion 7 and the female thread portion 8 of the go-side thread measuring portion 3 or the male thread portion 12 and the female thread portion 13 of the not-go-side thread measuring portion 5 of the thread plug gauge body a to form a concave shape which has a depth of 0.3 μm to 0.4 μm and a diameter of 2 mm and is blackened.

Note that printing on a ceramic material is performed by a special printing method such as laser marking.

Effects of the Invention

The first aspect of the invention provides a thread plug gauge with a maintenance line or the like in which in a thread plug gauge body having a go-side thread measuring portion extending from one side of a shank portion coaxially with the shank portion or a not-go-side thread measuring portion extending from the other side of the shank portion coaxially with the shank portion, a wear checking gauge line having a predetermined length and a predetermined depth or a round point, having a predetermined depth and a predetermined diameter is formed on a male thread portion and a female thread portion formed on the go-side thread measuring portion or the not-go-side thread measuring portion. Accordingly, as the various types of products are repeatedly threaded forward and backward into and from the go-side thread measuring portion or not-go-side thread measuring portion of the thread plug gauge, the wear checking gauge line wears out and disappears. Therefore, the first aspect of the invention has a merit of allowing the user to visually check the limits of the thread gauge and reliably know the time for replacement of the plug gauge.

In addition, the first aspect of the present invention allows the user to properly replace the thread plug gauge as the wear checking gauge line or the like wears out and disappears as described above, and hence has a merit of being capable of producing a test object with high accuracy and preventing the production of defective products.

The second aspect of the invention provides a thread plug gauge with a maintenance line or the like in which the wear checking gauge line formed on the male thread portion and the female thread portion of the go-side thread measuring portion or the not-go-side thread measuring portion has a linear shape. The second aspect of the invention therefore has the same effects as those of the first aspect of the invention defined in claim 1.

The third aspect of the invention provides a thread plug gauge with a maintenance line or the like in which the wear checking gauge line is printed on the male thread portion and the female thread portion so as to have a depth of 0.3 μm to 0.4 μm and a width of 0.2 mm. The third aspect of the invention therefore has the same effects as those of the first aspect of the invention.

The fourth aspect of the invention provides a thread plug gauge with a maintenance line or the like in which the round point is printed on the male thread portion and the female thread portion so as to have a depth of 0.3 μm to 0.4 μm and a diameter of 2 mm. The fourth aspect of the invention therefore has the same effects as those of the first aspect of the invention defined in claim 1.

The fifth aspect of the invention provides a thread plug gauge with a maintenance line or the like in which the thread plug gauge with the maintenance line or the like is formed by using alloy tool steel, a ceramic material, or a superhard material. The fifth aspect of the invention therefore has the same effects as those of the first aspect of the invention.

The sixth aspect of the invention provides a method of manufacturing a thread plug gauge with a maintenance line or the like, comprising connecting a thread plug gauge body to a negative electrode base connected to a power supply box which controls a current, setting a green stencil which has a cut-out portion having a desired marking pattern and from which an electrolytic solution exudes on a carbon filter with the electrolytic solution being contained in a positive electrode handle connected to the power supply box, energizing the set positive electrode handle while gripping the handle, and forming a wear checking gauge line on a male thread portion and a female thread portion of a go-side thread measuring portion or a male thread portion and a female thread portion of a not-go-side thread measuring portion of the thread plug gauge body by performing a marking process by sliding the positive electrode handle on the male thread portion and the female thread portion of the go-side thread measuring portion or the male thread portion and the female thread portion of the not-go-side thread measuring portion of the thread plug gauge body to form a concave shape which has a depth of 0.3 μm to 0.4 μm and a width of 0.2 mm and is blackened, or connecting a thread plug gauge body to a negative electrode base connected to a power supply box which controls a current, setting a green stencil which has a cut-out portion having a desired marking pattern and from which an electrolytic solution exudes on a carbon filter with the electrolytic solution being contained in a positive electrode handle connected to the power supply box, energizing the set positive electrode handle while gripping the handle, and forming a wear checking round point on a male thread portion and a female thread portion of a go-side thread measuring portion or a male thread portion and a female thread portion of a not-go-side thread measuring portion of the thread plug gauge body by performing a marking process without sliding the positive electrode handle on the male thread portion and the female thread portion of the go-side thread measuring portion or the male thread portion and the female thread portion of the not-go-side thread measuring portion of the thread plug gauge body to form a concave shape which has a depth of 0.3 μm to 0.4 μm and a diameter of 2 mm and is blackened. The sixth aspect of the invention has a merit of being capable of very reliably and quickly producing a wear checking gauge line which can reliably inform the time for replacement of the thread plug gauge, and thus has having the same effects as those of the first aspect of the invention.

The seventh aspect of the invention provides a thread ring gauge with a maintenance line or the like in which in a thread ring gauge body having an upper surface portion and a lower surface portion and having a go-side thread measuring portion formed on an inside portion to have a male thread portion and a female thread portion of the same class as that of a screw to be measured or having a not-go-side thread measuring portion formed on an inside portion to have a male thread portion and a female thread portion of the same class as that of a screw to be measured, wear checking gauge lines each having a predetermined length and a predetermined depth or round points each having a predetermined depth and a predetermined diameter are formed on male thread portions and female thread portions of the go-side thread measuring portion and the not-go-side thread measuring portion which are engraved in an inside portion between the upper surface portion and the lower surface portion which constitute one of the thread ring gauge bodies. Accordingly, the seventh aspect of the invention therefore has a merit of allowing the user to visually check the limits of the thread gauge by letting the wear checking gauge line wear out and disappear and to reliably know the time for replacement of the thread ring gauge.

In addition, the seventh aspect of the present invention allows the user to properly replace the thread ring gauge as the wear checking gauge line wears out as described above, and hence has a merit of being capable of producing a test object with high accuracy and preventing the production of defective products.

The eight aspect of the invention provides a thread ring gauge with a maintenance line or the like in which the wear checking gauge line of the seventh aspect of the invention has a linear shape. The eighth aspect of the invention therefore has the same effects as those of the seventh aspect of the invention.

The ninth aspect of the invention provides a thread ring gauge with a maintenance line or the like in which the wear checking gauge line of the seventh aspect of the invention is printed on the male thread portion and the female thread portion so as to have a depth of 0.3 μm to 0.4 μm and a width of 0.2 mm. The ninth aspect of the invention therefore has the same effects as those of the seventh aspect of the invention.

The tenth aspect of the invention provides a thread plug gauge with a maintenance line or the like in which the round point of the sixth aspect of the invention is printed on the male thread portion and the female thread portion so as to have a depth of 0.3 μm to 0.4 μm and a diameter of 2 mm. The tenth aspect of the invention therefore has the same effects as those of the sixth aspect of the invention.

The eleventh aspect of the invention provides a thread ring gauge with a maintenance line or the like in which the thread ring gauge body is formed by using alloy tool steel, a ceramic material, or a superhard material. The eleventh aspect of the invention therefore has the same effects as those of the seventh aspect of the invention.

The twelfth aspect of the invention provides a method of manufacturing a thread ring gauge with a maintenance line or the like, characterized by comprising connecting a thread ring gauge body to a negative electrode base connected to a power supply box which controls a current, setting a green stencil which has a cut-out portion having a desired marking pattern and from which an electrolytic solution exudes on a carbon filter with the electrolytic solution being contained in a positive electrode handle connected to the power supply box, energizing the set positive electrode handle while gripping the handle, and forming a wear checking gauge line on a male thread portion and a female thread portion of a go-side thread measuring portion or a male thread portion and a female thread portion of a not-go-side thread measuring portion of the thread ring gauge body by performing a marking process by sliding the positive electrode handle on the male thread portion and the female thread portion of the go-side thread measuring portion or the male thread portion and the female thread portion of the not-go-side thread measuring portion to form a concave shape which has a depth of 0.3 μm to 0.4 μm and a width of 0.2 mm and is blackened, or connecting a thread ring gauge body to a negative electrode base connected to a power supply box which controls a current, setting a green stencil which has a cut-out portion having a desired marking pattern and from which an electrolytic solution exudes on a carbon filter with the electrolytic solution being contained in a positive electrode handle connected to the power supply box, energizing the set positive electrode handle while gripping the handle, and forming a wear checking round point on a male thread portion and a female thread portion of a go-side thread measuring portion or a male thread portion and a female thread portion of a not-go-side thread measuring portion of the thread ring gauge body by performing a marking process without sliding the positive electrode handle on the male thread portion and the female thread portion of the go-side thread measuring portion or the male thread portion and the female thread portion of the not-go-side thread measuring portion of the thread ring gauge body to form a concave shape which has a depth of 0.3 μm to 0.4 μm and a diameter of 2 mm and is blackened. The twelfth aspect of the invention has a merit of being capable of very reliably and quickly producing a wear checking gauge line or the like which can reliably inform the time for replacement of the thread ring gauge, and thus has the same effects as those of the seventh aspect of the invention.

BRIEF DESCRIPTION OF THE DRAWINGS

FIG. 1 is a front view of a thread plug gauge body with a maintenance line or the like of a limit thread gauge according to the present invention.

FIG. 2 is a partially cutaway enlarged perspective view of the go-side thread measuring portion of the plug gauge in FIG. 1.

FIG. 3 is a partially cutaway enlarged perspective view of the not-go-side thread measuring portion of the thread plug gauge in FIG. 1.

FIG. 4 is a perspective view of the go-side thread measuring portion of the thread plug gauge in FIG. 1 before inspection.

FIG. 5 is a perspective view showing a state of the go-side thread measuring portion of the thread plug gauge in FIG. 4 at the time of inspection.

FIG. 6 is a perspective view showing a state at the completion of inspection in FIG. 5.

FIG. 7 is a perspective view showing a state of the not-go-side thread measuring portion of the thread plug gauge in FIG. 1 immediately before the measuring portion is threaded into a test object.

FIG. 8 is a perspective view showing a state immediately before inspection relative to the state in FIG. 7.

FIG. 9 is a perspective view showing a state when inspection starts from the state in FIG. 8.

FIG. 10 is a perspective view of the go-side thread measuring portion of a thread ring gauge set with a maintenance line or the like according to the present invention.

FIG. 11 is a perspective view of the not-go-side thread measuring portion of a thread ring gauge set with a maintenance line or the like according to the present invention.

FIG. 12 is a front view of a go-side thread measuring portion in FIG. 10.

FIG. 13 is a front view of a not-go-side thread measuring portion in FIG. 11.

FIG. 14 is a longitudinal front sectional view of the go-side thread measuring portion in FIG. 10.

FIG. 15 is a perspective view showing a state of the go-side thread measuring portion shown in FIG. 10 immediately before the measuring portion is threaded into a test object.

FIG. 16 is a perspective view showing an inspection state in which the measuring portion in the state in FIG. 15 is threaded into the test object.

FIG. 17 is a perspective view showing a state when the state in FIG. 16 is viewed from the opposite side.

FIG. 18 is a perspective view showing a state of the not-go-side thread measuring portion of the thread ring gauge set with the maintenance line or the like in FIG. 11 immediately before the measuring portion is threaded into a test object.

FIG. 19 is a perspective view showing a state in which the not-go-side thread measuring portion FIG. 18 is threaded into the test object.

FIG. 20 is a perspective view showing a state when the state in FIG. 19 in which the measuring portion is threaded into the test object is viewed from the opposite side.

FIG. 21 is a perspective view showing a state immediately before the formation a gauge line on the go-side thread measuring portion of the thread plug set shown in FIG. 1.

FIG. 22 is a perspective view showing a state in which a positive electrode handle in FIG. 21 is brought into contact with an end portion of the go-side thread measuring portion.

FIG. 23 is a perspective view showing a state in which the positive electrode handle in the state shown in FIG. 21 is slightly slid in the direction of a shank portion.

FIG. 24 is a perspective view showing a state in which the positive electrode handle in the state in FIG. 23 is slid in the direction of the shank portion.

FIG. 25 is a perspective view of the go-side thread measuring portion on which a wear checking gauge line is printed in the process from the state in FIG. 21 to the state in FIG. 24.

BEST MODE FOR CARRYING OUT THE INVENTION

The modes for carrying out the first through twelfth aspects of the invention are common, and hence will be collectively described below.

Referring to the accompanying drawings, reference symbol a denotes the thread plug gauge body of a thread plug gauge having a set of a go-side thread measuring portion and a not-go-side thread measuring portion coaxially extending from the left and right two sides of the shank portion of the thread gauge referred to as the thread gauge. The thread plug gauge body has the following arrangement.

The thread plug gauge body a has a prismatic shank portion 1 in the middle portion. A left constricted portion. 2 extends from the left side of the shank portion 1. A go-side thread measuring portion 3 extends from the left side of the constricted portion 2.

A right constricted portion 4 extends from the right side of the shank portion 1. A not-go-side thread measuring portion 5 extends from the right side of the right constricted portion 4.

The shank portion 1, the left and right two constricted portions 2 and 4, the go-side thread measuring portion 3, and the not-go-side thread measuring portion 5 are coaxially formed.

As shown in FIG. 1, the present invention forms the go-side thread measuring portion 3 and the not-go-side thread measuring portion 5 as a set on the left and right two sides of the shank portion 1, and uses the resultant structure as a limit thread plug set. However, the go-side thread measuring portion 3 or the not-go-side thread measuring portion 5 may coaxially extend from one side of the shank portion 1, as described above.

The shank portion 1 generally has a hexagonal prismatic shape but is not limited to it.

There are many types of thread gauges, other than those shown in the accompanying drawings, which allow wear checking gauge lines to be printed on the male and female thread portions of thread measuring portions, which the spirit of the present invention includes. For example, such gauges include, when a test object is a female screw, a gauge having a go-side thread measuring portion formed on one side of the shank portion 1, a gauge having a not-go-side thread measuring portion formed on one side of the shank portion 1, a gauge having an inspection not-go-side thread measuring portion formed on one side of the shank portion. 1, and a gauge having a working not-go-side thread measuring portion or the like formed on one side of the shank portion 1. When a test object is a male screw, such gauges include a go-side thread, ring gauge, not-go-side thread ring gauge, inspection not-go-side thread ring gauge, and working not-go-side thread ring gauge. When a test object to be inspected is a thread plug gauge, such gauges include a go-side wear checking thread ring gauge, not-go-side wear checking thread ring gauge, go-side wear checking thread ring gauge, inspection not-go-side wear checking thread ring gauge, and working not-go-side sear checking ring gauge. When a target object to be inspected is a thread ring gauge, such gauges include a go-side wear checking thread ring gauge, inspection not-go-side wear checking thread plug gauge, and working not-go-side wear checking thread plug gauge.

As shown in the accompanying drawings, the go-side thread measuring portion 3 has a thread having a predetermined length helically engraved such that male thread portions (thread crests) 7 and female thread portions (thread roots) 8 are alternately formed.

Referring to the accompanying drawings, reference numeral 9 denotes a wear checking gauge line having a depth of 0.3 μm to 0.4 μm and a width of 0.2 mm, which is formed by printing processing on the male thread portions 7 and the female thread portions 8 between an end portion 6 of the go-side thread measuring portion 3 and the left constricted portion 2. Although the length of the wear checking gauge line 9 generally covers all the male thread portions 7 and the female thread portions 8 between the end portion 6 of the go-side thread measuring portion 3 and the left constricted portion 2, printing processing may be applied to some of the male thread portions 7 and the female thread portions 8.

The wear checking gauge line 9 is generally linear but is not limited to this.

In the present invention, a wear checking gauge line which is identical to the wear checking gauge line 9 and has a depth of 0.3 μm to 0.4 μm and a width of 0.2 mm is formed on male thread portions (thread crests) 12 and female thread portions (thread roots) 13 formed between an end portion 10 of the not-go-side thread measuring portion 5 and the right constricted portion 4 by printing processing.

Although the length of the wear checking gauge line 14 generally covers all the male thread portions 12 and the female thread portions 13 between the end portion 10 of the not-go-side thread measuring portion 5 and the right constricted portion 4, printing processing may be applied to some of the male thread portions 12 and female thread portions 13.

The wear checking gauge line 14 is generally linear but is not limited to this.

The prismatic shank portion 1, the left and right two constricted portions 2 and 4, the go-side thread measuring portion 3, and the not-go-side thread measuring portion 5 are coaxially formed.

The thread plug gauge with the maintenance line or the like, which is constituted by the prismatic shank portion 1, the two constricted portions 2 and 4, the go-side thread measuring portion 3, and the not-go-side thread measuring portion 5, is formed by using alloy tool steel, a ceramic material, a superhard material, or the like.

The following will describe a printing processing method according to the spirit of the present invention, which is performed to print the wear checking gauge lines 9 and 14 on the male thread portions 7 and 12 and the female thread portions 8 and 13 forming the go-side thread measuring portion. 3 and not-go-side thread measuring portion 5 of the thread plug gauge body a.

That is, this method uses a power supply box d which controls a current.

A negative electrode base is connected to the power supply box d.

A positive electrode handle is further connected to the power supply box d.

The thread plug gauge body a is connected to the negative electrode base.

A green stencil which has a cut-out portion having a desired marking pattern and from which an electrolytic solution exudes is then set on a carbon filter with the electrolytic solution being contained in a positive electrode handle connected to the power supply box d.

Note that printing on a ceramic material is performed by a special printing method such as laser marking.

While the user grips the positive electrode handle set in the above manner, the handle is energized and slid on the surfaces of the male thread portions 7 and female thread portions 8 of the go-side thread measuring portion 3 of the thread plug gauge body a and the surfaces of the male thread portions 12 and female thread portions 13 of the not-go-side thread measuring portion 5.

As described above, the positive electrode handle is applied to the go-side thread measuring portion 3 such that the positive electrode handle is kept still in contact with the surfaces of each male thread portion 7 and each female thread portion 8 for about 2 sec and slid from a side of the end portion 6, on which neither male thread portions 7 nor female thread portions 8 are formed, in the direction of the constricted portion 2.

As a result, a marking process is performed to form the above wear checking gauge line on the surfaces of the male thread portions 7 and female thread portions 8 by forming a concave shape which has a depth of 0.3 μm to 0.4 μm and a width of 0.2 mm and is blackened.

In addition, the wear checking gauge line 14 is formed on the surfaces of the male thread portions 12 and female thread portions 13 of the not-go-side thread measuring portion 5 on the not-go side of the thread plug gauge body a by a technique similar to the above marking process step of forming the wear checking gauge line 9 on the surfaces of the male thread portions 7 and female thread portions 8 of the go-side thread measuring portion 3.

However, a slight difference between these techniques is that the positive electrode handle connected to the power supply box d is kept still in contact with the surfaces of each male thread portion 12 and each female thread portion 13 for about 2 sec and slid from the end portion 10 of the not-go-side thread measuring portion 5 in the direction of the right constricted portion 4.

The above description is about the printing process step for the wear checking gauge line of the thread gauge with the maintenance line or the like according to the present invention.

Reference symbol b denotes a thread ring set body which measures the go side of a thread product 26 and has the following arrangement.

The thread ring set body b has an upper surface portion 15 and a lower surface portion 16. The thread ring set body b also has, on an inside portion 17, a go-side thread measuring portion 20 having male thread portions 18 and female thread portions 19 of the same class as that of a screw to be measured.

Reference symbol c denotes a thread ring set body which measures the not-go side of a thread product 27 and has the following arrangement.

The thread ring set body c has an upper surface portion 15 and a lower surface portion 16 and also has a not-go-side thread measuring portion 23 having, on an inside portion 17, male thread portions 21 and female thread portions 22 of the same class as that of a screw to be measured.

Reference numeral 24 denotes a wear checking gauge line which is provided on the go-side thread measuring portion 20 described above and has the following arrangement.

That is, the gauge line 24 having a depth of 0.3 μm to 0.4 μm and a width of 0.2 mm is formed by printing on the male thread portions 18 and female thread portions 19 of the go-side thread measuring portion 20 which are engraved between the upper surface portion 15 and the lower surface portion 16 which constitute the thread ring set body b. The gauge line 24 is generally linear but is not limited to this.

Note that printing on a ceramic material is performed by a special printing method such as laser marking.

Reference numeral 25 denotes a wear checking gauge line which is provided on the not-go-side thread measuring portion 23 described above and has the following arrangement.

That is, the gauge line 25 having a depth of 0.3 μm to 0.4 μm and a width of 0.2 μm is formed by printing on the male thread portions 21 and female thread portions 22 of the not-go-side thread measuring portion 23 which are engraved between the upper surface portion 15 and the lower surface portion 16 which constitute the thread ring set body c. The gauge line 25 is generally linear but is not limited to this.

The limit thread ring gauge bodies b and c are formed by using alloy tool steel, a ceramic material, or a superhard material.

The following will describe a method of manufacturing the wear checking gauge line 24 or 25 on the male thread portions 18 and female thread portions 19 of the go-side thread measuring portion 20 of the thread ring gauge body b or the male thread portions 21 and female thread portions 22 of the not-go-side thread measuring portion 23 of the thread ring gauge body c.

In order to form the wear checking gauge line 24 or 25 on the male thread portions 18 and female thread portions 19 of the go-side thread measuring portion 20 of the thread ring gauge body b or the male thread portions 21 and female thread portions 22 of the not-go-side thread measuring portion 23 of the thread ring gauge body c, first of all, the thread ring gauge body b or c is connected to the negative electrode base connected to the power supply box d which controls a current, and a green stencil which has a cut-out portion having a desired marking pattern and from which an electrolytic solution exudes is then set on a carbon filter with the electrolytic solution being contained in a positive electrode handle connected to the power supply box d. While the user grips the positive electrode handle set in the above manner, the handle is energized and slid on the male thread portions 18 and female thread portions 19 of the go-side thread measuring portion 20 or the male thread portions 21 and female thread portions 22 of the not-go-side thread measuring portion 23. As a result, a marking process is performed to form the wear checking gauge line 24 or 25 on the surface portions of one set of the male thread portions 18 and female thread portions 19 or the other set of the male thread portions 21 and female thread portions 22 by forming a concave shape which has a depth of 0.3 μm to 0.4 μm and a width of 0.2 mm and is blackened.

The above description is about the printing process step for the wear checking gauge line of the thread ring set body b or c with the maintenance line or the like according to the present invention.

The usage of the thread gauge with the maintenance line or the like according to the present invention will be further described below.

The usage of the thread plug set body a will be described first.

The go-side thread measuring portion 3 forming the thread plug gauge body a is threaded into a female thread 27 of the test object 26 stepwise from FIG. 4 to FIG. 5 and from FIG. 5 to FIG. 6, and is then threaded backward.

As gauge measurement is continuously repeated between the go-side thread measuring portion 3 and the test object 26 in the process shown in the above drawings and the female thread 27 of the test object 26 makes frequent contact with the male thread portions 7 and female thread, portions 8 of the go-side thread measuring portion 3, the wear checking gauge line 9 formed on the male thread portions 7 and female thread portions 8 of the go-side thread measuring portion. 3 gradually disappears due to the contact.

As the wear checking gauge line 9 disappears through a gauge process like that described above, the user can reliably check and know the predetermined upper and lower limits of dimensional accuracy of a thread product. This makes it possible to reliably know the time for replacement of the thread gauge.

The usage of the not-go-side thread measuring portion 5 of the thread plug gauge body a is to repeatedly thread forward and backward the not-go-side thread measuring portion 5 into and from the female thread 27 of the test object 26 by the same method as the conventional gauge method, as shown in FIGS. 7, 8, and 9.

As gauge measurement is repeated between the test object 26 and the not-go-side thread measuring portion 5 and the female thread 27 of the test object 26 makes frequent contact with the male thread portions 12 and female thread portions 13 of the not-go-side thread measuring portion 5, the wear checking gauge line 14 formed on the male thread portions 12 and female thread portions 13 of the not-go-side thread measuring portion 5 gradually disappears due to the contact.

As the wear checking gauge line 14 disappears through a gauge process like that described above, the user can reliably check and know the predetermined upper and lower limits of dimensional accuracy of a thread product. This makes it possible to reliably know the time for replacement of the thread gauge.

The usage of the thread ring set body b of the ring gauge with the maintenance line or the like according to the present invention will be described below.

The usage of the ring gauge body b is to repeatedly thread forward and backward male thread 28 of the test object 26 into and from the go-side thread measuring portion 20 of the thread ring set body b, as shown in FIGS. 15, 16, and 17.

For this reason, as the male thread 28 of the test object 26 makes frequent contact with the male thread portions 18 and female thread portions 19 of the go-side thread measuring portion 20, the wear checking gauge line 24 formed on the male thread portions 18 and female thread portions 19 of the go-side thread measuring portion 20 of the thread ring gauge body b gradually disappears due to the contact.

When the wear checking gauge line 24 disappears as described above, the user can reliably check and know the predetermined, upper and lower limits of dimensional accuracy of a thread product. This makes it possible to reliably know the time for replacement of the thread gauge.

The usage of the thread ring set body c of the thread gauge with the maintenance line or the like according to the present invention will be described below.

The usage of the ring gauge body c is to repeatedly thread forward and backward male thread 29 of a test object 28 into and from the not-go-side thread measuring portion 23 of the thread ring gauge body c, as shown in FIGS. 18, 19, and 20.

For this reason, the male thread 29 of the test object 28 makes frequent contact with the male thread portions 21 and female thread portions 22 of the not-go-side thread measuring portion 23. As a consequence, the wear checking gauge line 25 formed on the male thread portions 21 and female thread portions 22 of the not-go-side thread measuring portion 23 of the thread ring gauge body c gradually disappears due to the contact.

When the wear checking gauge line 25 disappears as described above, the user can reliably check and know the predetermined upper and lower limits of dimensional accuracy of a thread product. This makes it possible to reliably know the time for replacement of the thread gauge.

The round point is not shown in the accompanying drawings, as it is determined that the textual explanation suffices.

REFERENCE SIGNS LIST a thread plug gauge body
b thread ring gauge body
c thread ring gauge body
d power supply box
1 shank portion
2 constricted portion
3 thread measuring portion
4 constricted portion
5 not-go-side thread measuring portion
6 end portion
7 male thread portion
8 female thread portion
9 wear checking gauge line
10 end portion
12 male thread portion
13 female thread portion
14 wear checking gauge line
15 upper surface portion
16 lower surface portion
17 inside portion
18 male thread portion
19 female thread portion
20 go-side thread measuring portion
21 male thread portion
22 female thread portion
23 not-go-side thread measuring portion
24 wear checking gauge line
25 wear checking gauge line
26 test object
27 female thread
28 male thread
29 male thread portion

What is claimed is:
1. A thread ring gauge with a maintenance line, the thread ring gauge comprising:

at least one thread ring gauge body having an upper surface portion and a lower surface portion and having a go-side thread measuring portion formed on an inside portion to have a male thread portion and a female thread portion of the same class as that of a screw to be measured or having a not-go-side thread measuring portion formed on an inside portion to have a male thread portion and a female thread portion of the same class as that of a screw to be measured; and at least one wear checking gauge line having a predetermined length and a predetermined depth or at least one round point having a predetermined depth and a predetermined diameter formed on the male thread portion and female thread portion of the go-side thread measuring portion and the not-go-side thread measuring portion which are engraved between the upper surface portion and the lower surface portion which constitute the at least one of the thread ring gauge body.

2. The thread ring gauge with the maintenance line according to claim 1, wherein the at least one wear checking gauge line has a linear shape.

3. The thread ring gauge with the maintenance line according to claim 1, wherein the at least one wear checking gauge line is printed on the male thread portion and the female thread portion so as to have a depth of 0.3 μm to 0.4 μm and a width of 0.2 mm.

4. The thread ring gauge with the maintenance line according to claim 1, wherein the at least one round point is printed on the male thread portion and the female thread portion so as to have a depth of 0.3 μm to 0.4 μm and a diameter of 2 mm.

5. The thread ring gauge with the maintenance line according to claim 1, wherein the thread ring gauge body is formed by using alloy tool steel, a ceramic material, or a superhard material.

* * * * *